(12) United States Patent
Royyuru et al.

(10) Patent No.: US 8,999,130 B2
(45) Date of Patent: *Apr. 7, 2015

(54) FIELD EFFECT BASED NANOSENSOR FOR BIOPOLYMER MANIPULATION AND DETECTION

(71) Applicant: International Business Machines Corporation, Armonk, NY (US)

(72) Inventors: Ajay K. Royyuru, Congers, NY (US); Chao Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/969,997

(22) Filed: Aug. 19, 2013

(65) Prior Publication Data
US 2014/0151228 A1   Jun. 5, 2014

Related U.S. Application Data

(63) Continuation of application No. 13/690,149, filed on Nov. 30, 2012.

(51) Int. Cl.
*G01N 27/447* (2006.01)
*G01N 33/68* (2006.01)
*B82Y 15/00* (2011.01)
(Continued)

(52) U.S. Cl.
CPC .......... *G01N 27/44791* (2013.01); *B82Y 15/00* (2013.01); *B82Y 30/00* (2013.01); *G01N 27/414* (2013.01); *G01N 33/48721* (2013.01); *Y10S 977/962* (2013.01); *Y10S 977/733* (2013.01); *G01N 33/68* (2013.01); *Y10S 977/853* (2013.01);
(Continued)

(58) Field of Classification Search
CPC . G01N 27/447; G01N 27/4473; G01N 33/68; Y10S 977/853; Y10S 977/733; Y10S 977/962; Y10S 977/832; B82Y 15/00; B82Y 30/00
USPC ................ 435/6.1, 287.1; 422/82.01, 68.1; 204/450; 977/924, 962
See application file for complete search history.

(56) References Cited

U.S. PATENT DOCUMENTS 5,795,782 A   8/1998   Church et al.
7,947,485 B2   5/2011   Wu et al.
(Continued)

FOREIGN PATENT DOCUMENTS

WO   WO2012006657 A1   1/2012

OTHER PUBLICATIONS

Branton et al., "The Potential and Challenges of Nanopore Sequencing," 2008 Nature Biotechnology, vol. 26, No. 10, 1146-53, 8 pages.
(Continued)

*Primary Examiner* — Jennifer Dieterle
(74) *Attorney, Agent, or Firm* — Cantor Colburn LLP; Vazken Alexanian

(57) ABSTRACT

A mechanism is provided for manipulating a molecule. The molecule is driven into a nanochannel filed with electrically conductive fluid. A first vertical electric field is created inside the nanochannel to slow down the molecule and/or immobilize the molecule. The molecule is stretched into non-folded linear chains by the first vertical electric field and a horizontal electric field. Monomers of the molecule are sequentially read.

14 Claims, 16 Drawing Sheets

(51) Int. Cl.
*B82Y 30/00* (2011.01)
*G01N 27/414* (2006.01)
*G01N 33/487* (2006.01)

(52) U.S. Cl.
CPC ........... *Y10S 977/832* (2013.01); *G01N 27/447* (2013.01)

(56) References Cited

U.S. PATENT DOCUMENTS

| | | | |
|---|---|---|---|
| 8,013,366 | B2 | 9/2011 | Lee et al. |
| 2007/0048745 | A1* | 3/2007 | Joyce et al. ............... 435/6 |
| 2007/0063304 | A1 | 3/2007 | Matsumoto et al. |
| 2007/0292855 | A1 | 12/2007 | Dubin et al. |
| 2008/0187915 | A1* | 8/2008 | Polonsky et al. ........... 435/6 |
| 2009/0066315 | A1* | 3/2009 | Hu et al. ................. 324/71.4 |
| 2010/0066348 | A1 | 3/2010 | Merz et al. |
| 2010/0096268 | A1* | 4/2010 | Ling et al. ................ 204/549 |
| 2010/0248284 | A1 | 9/2010 | Chen et al. |
| 2010/0327255 | A1* | 12/2010 | Peng et al. ................. 257/9 |
| 2011/0114573 | A1 | 5/2011 | Simpson et al. |
| 2011/0192724 | A1 | 8/2011 | Han et al. |
| 2011/0217544 | A1 | 9/2011 | Young et al. |
| 2011/0227558 | A1* | 9/2011 | Mannion et al. ........... 324/71.1 |
| 2011/0236984 | A1* | 9/2011 | Sun et al. ................. 436/94 |
| 2012/0138460 | A1 | 6/2012 | Baghbani-Parizi et al. |
| 2012/0228556 | A1 | 9/2012 | Roundhill |
| 2012/0241391 | A1 | 9/2012 | Carlson et al. |
| 2012/0255899 | A1 | 10/2012 | Choi et al. |

OTHER PUBLICATIONS

Cao et al, "Fabrication of 10 nm Enclosed Nanofluidic Channels," Applied Physics Letters, vol. 81, No. 1, Jul. 1, 2002, Applied Physics Letters 81 174-6.

J. Clarke et al., "Continuous Base Identificaton for Single-molecule Nanopore DNA Sequencing," Nature Nanotechnology, vol. 4, 2009, pp. 265-270.

Dekker, "Solid-State Nanopores," 2007 Nature Nanotechnology, vol. 2, 209-15, 7 pages.

Firnkes M, Pedone D, Knezevic J, Doblinger M and Rant U, "Electronically Facilitated Translocations of Proteins through Silicon Nitride Nanopores: Conjoint and Competitive Action of Diffusion, Electrophoresis, and Electroosmosis," 2010 Nano Letters 10 2162-7.

Fu J P, Schoch R B, Stevens A L, Tannenbaum S R and Han J Y, "A Patterned Anisotripic Nanofluidic Sieving Structure for Continuous-flow Seperation of DNA and Proteins," 2007 Nature Nanotechnology, vol. 2, www.nature.com/naturenanotechnology; 8 pages.

M. Gershow et al,, "Recapturing and Trapping Single Molecules with a Solid-state Nanopore," Nature Nanotechnology, vol. 2, 2007, pp. 775-779.

S. Huang et al., "Identifying Single Bases in a DNA Oligomer with Electron Tunnelling," Nature Nanotechnology, vol. 5, 2010, pp. 868-873.

X. Liang et al., "Nanogap Detector Inside Nanofluidic Channel for Fast Real-Time Label-Free DNA Analysis," Nano Lett., vol. 8, No. 5, 2008, pp. 1472-1476.

Meller A, Nivon L and Branton D 2001 Physical Review Letters 86 3435-8.

Reisner W, Morton K J, Riehn R, Wang Y M, Yu Z N, Rosen M, Sturm J C, Chou S Y, Frey E and Austin R H, "Statics and Dynamics of Single DNA Molecules Confined in Nanochannels," 2005 Phys. Rev. Lett. 94, 4 pages.

Tanaka H and Kawai T, "Partial Sequencing of a Single DNA Molecule with a Scanning Tunnelling Microscope," 2009 Nature Nanotechnology 4 518-22, 5 pages.

Tegenfeldt J O, Prinz C, Cao H, Chou S, Reisner W W, Riehn R, Wang Y M, Cox E C, Sturm J C, Silberzan P and Austin R H, "The Dynamics of Genomic-length DNA Molecules in 100-nm Channels," 2004 Proceedings of the National Academy of Sciences of the United States of America 101 10979-83, 5 pages.

International Search Report dated Jan. 13, 2014; International Application No. PCT/US13/54822 filed Aug. 14, 2013; pp. 1-20.

Written Opinion of the International Searching Authority dated Jan. 13, 2014; International Application No. PCT/US13/54822 filed Aug. 14, 2013; pp. 1-6.

* cited by examiner

FIELD EFFECT BASED NANOSENSOR FOR BIOPOLYMER MANIPULATION AND DETECTION

CROSS REFERENCE TO RELATED APPLICATIONS

The present application is a continuation of U.S. patent application Ser. No. 13/690,149, entitled "FIELD EFFECT BASED NANOSENSOR FOR BIOPOLYMER MANIPULATION AND DETECTION", filed on Nov. 30, 2012, which is incorporated herein by reference in its entirety.

BACKGROUND

The present invention relates to nanopore/nanotrench devices, and more specifically, to control of molecules in nanopore/nanotrench devices.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method for manipulating a molecule is provided. The method includes driving the molecule into a nanochannel filed with electrically conductive fluid, and creating a first vertical electric field inside the nanochannel to slow down the molecule and/or immobilize the molecule. Also, the method includes stretching the molecule into non-folded linear chains by the first vertical electric field and a horizontal electric field, and sequentially reading monomers of the molecule.

According to an embodiment, a system for manipulating a molecule is provided. The system includes a nanochannel filled with electrically conductive fluid, in which the molecule is driven into the nanochannel. A first pair of trapping electrodes are positioned to the nanochannel, and the first pair of trapping electrodes are configured to create a first vertical electric field inside the nanochannel to slow down the molecule and/or immobilize the molecule. The first pair of trapping electrodes are configured to stretch the molecule into non-folded linear chains by the first vertical electric field and a horizontal electric field. A pair of sensing electrodes are positioned to the nanochannel, and the pair of sensing electrodes are configured to sequentially read monomers of the molecule.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 4A through 4C illustrate a process of the metal insulator channel field effect transistor (MIC-FET) device for controlling the molecule and for electrical tunneling sequencing according to an embodiment, in which:

FIG. 4A shows cross-sectional views for trapping and straightening the molecule utilizing one trap;

FIG. 4B shows cross-sectional views for trapping with two traps, continuing to straighten the molecule, and sequencing the molecule base by base;

FIG. 4C shows moving the molecule out to sequence the next molecule.

FIGS. 5A through 5E illustrate a fabrication process for the metal insulator channel field effect transistor (MIC-FET) device according to an embodiment, in which:

FIG. 5A is a top view of fabricating nanotrenches in the substrate;

FIG. 5B is a top view of which illustrates reducing the trench size by conformal dielectric deposition to form the nanochannel;

FIG. 5C is a top view which illustrates deposition of metals M1, M2, and M3 over the nanochannel;

FIG. 5D is a top view which illustrates sealing of the nanochannel with a top-gate dielectric material; and FIG. 5E is a top view which illustrates deposition of the top gate M4.

DETAILED DESCRIPTION

Figure 1A:
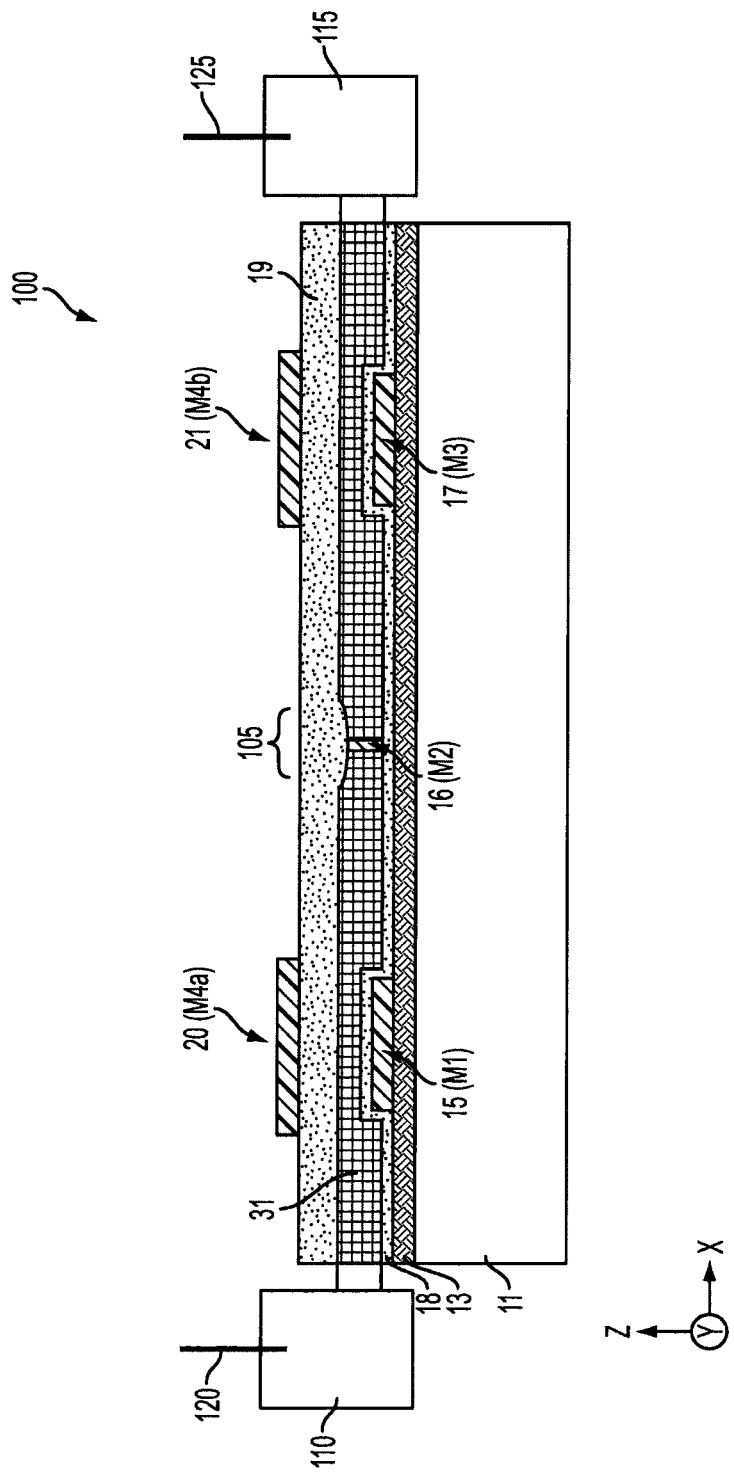
FIG. 1A is a cross-sectional view of a metal insulator channel field effect transistor (MIC-FET) device according to an embodiment.

An embodiment provides a system for sensing a charged biopolymer which includes using electrostatic force to drive charged biopolymer into a nanofluidic channel, creating an electrostatic field vertically inside the nanochannel to slow down and/or immobilize the biopolymer, stretching the biopolymer into non-folded linear chains, moving the biopolymer to a metallic nanogap, and sequential reading the signatures of monomers of the biopolymers.

Accurate and inexpensive sensing of biopolymers, especially nucleic acids (DNA, RNA), is important to understanding of many scientific and biomedical applications. A high-throughput and robust device to electrical sequence the biopolymers would be beneficial.

Biological nanopores have been utilized to detect polynucleotides by monitoring the ionic current levels as the molecules translocate through a 1-2 nm (nanometer) transmembrane channel in a lipid bilayer. Despite fast progress, the biological nanopores may suffer from a number of issues, such as restricted working conditions (temperature, voltage, and chemical environment), short device lifetime, slow production rate of nanopores, etc.

Solid-state bio-sensing techniques, such as artificial nanopores and channels, have been integrated into fluidics for sensing of many types of molecules, including DNA, RNA, proteins, etc. Although very promising in low-cost high-accuracy molecular detection, e.g. DNA sequencing, the current approaches still some particular elements missing: (1) well controlled geometry with a critical dimension down to a few nanometers for accurate molecular localization and sensing; (2) effective molecular trapping mechanism to accurately control the molecular location and speed; (3) an integrated sensor for accurate molecular tunneling recognition; (4) independent control and fast switch between molecular trapping and sensing; (5) a robust structure design to allow long shelf-time and working lifetime; (6) full compatibility with planar VLSI (very large scale integration) technique for large-scale production. A solid-state biosensor design integrating the above elements would be beneficial.

An embodiment provides techniques and systems based on solid-state planar nanochannel/nanotrench structures for biomolecule detection. The system integrates the biopolymer trapping, linearization, and tunneling sensing into a whole nanoscale fluidic system, where great flexibilities are maintained in the design of structural geometry, the selection of materials (electrode and dielectrics), and also compatibility with future on-chip circuits. The system integrates fluidic nanochannels with electrodes for both biopolymer motion-control and sensing. The sensing methods using both conventional ionic current and more accurate transverse tunneling current are available. The fabrication of the system can be entirely based on current CMOS (complementary metal oxide semiconductor) technologies, and is feasible for large-scale and high-throughput production.

Here, both a "nanotrench" and a "nanochannel" refer to one-dimensional volume with its depth and width well within the nanoscale (e.g., from a few nanometers to 100 nanometers) while its length is much larger (e.g., tens of nanometers to micrometers). For clarification, a "nanotrench" refers to a structure with the top open to the air, while a "nanochannel" refers to a top-sealed structure. In the applications of electrical sensing of biopolymers, a sealed nanochannel is considered a better platform, as the sealed nanochannel allows the integration with more functional elements (e.g., a top electrode as discussed herein), and also provides more reliable and accurate control of the biopolymers.

Further, the system provides linearization of polymer molecules (e.g., DNA, RNA, and protein) and sequential flow of individual monomers with a controlled velocity into a nano-confined space bearing tunneling sensing electrodes. A monomer is a molecule that may bind chemically to other molecules to form a polymer. The nano-confined nanochannel has a small diameter (e.g., smaller than 100 nanometers and particularly smaller than 20 nanometers) and has a sufficient length for uniform flow and high-throughput reading of long polymer segments. The nanochannel is equipped with vertical electrode pairs for immobilization, or referred as "trapping" here, of the target polymer at specific positions. The nanochannel also integrates with a series of lateral electrodes (e.g., along the nanochannel direction) for control of the polymer shape, speed, and position. The tunneling sensor is a split electrode junction embedded in the nanochannel with a nano-gap in between (e.g., smaller than 5 nanometer and particularly 1-3 nm).

As one feature, the polymers are immobilized by the vertical trapping electrodes before contacting the nanogap sensor. The vertical trapping electrodes include two sets of bottom electrodes at both the entrance and the exit of the nanochannel, and also two sets of top electrodes paired and aligned to the bottom electrodes. The paired top and bottom electrodes are separated by a dielectric layer, which encloses the fluidic channel.

The entry of charged polymer into the nanochannel causes subsequent change of the ionic current, which can trigger to apply an electric potential on the bottom and top electrodes and thus establish a vertical electric field in the nanochannel sandwiched between the electrodes.

For example, the electric field strength, and accordingly the force exerted on the DNA in the nanochannel, can be maximized by reducing the dielectric layer thicknesses between the electrodes and the nanochannel and by using a high-k dielectric material. With a large enough vertical electrostatic force, the polymer is pushed to the top ceiling or the bottom floor of the nanochannel and thus experiences a large friction force from the channel sidewall. The friction force can greatly slow down the polymer's moving velocity in the nanochannel and can even temporarily trap the polymer inside the nanochannel, given that the electrophoretic forces exerted by the external electrodes in the two micro-sized inlet/outlet and/or by the adjacent horizontal electrode pairs are much smaller than the friction force.

As one feature, the charged polymers are trapped and then linearized by the lateral trapping electrodes. With the vertical trapping field applied on the charged polymer, small DC or AC voltages are applied between the trapping electrodes and the inlets/outlets. The forces are designed so that the nontrapped polymers in the nanochannels are pushed out through the entrance or the exit. The electrostatic forces also pull on both sides of the trapped polymer, and essentially linearize the polymer.

As one feature, the sequential reading of the monomers, e.g., the bases for DNA and RNA, is accomplished by passing the linearized polymers, through a microscale inlet/outlet, into the nanochannels bearing the nanogap electrode sensor. The monomers are driven electrostatically by the horizontal electric field and forced to pass through the nanogap sensor linearly, resulting in tunneling current flow through the split sensing electrodes with the monomers working as a bridge.

As a feature, the split sensing electrode is functionalized with chemical linkers, which can selectively bond to the different monomers to be tested. As the monomers flow through the nanogap between the sensing electrodes, they bond to the linkers with different strengths and for different durations, hence giving rise to sensing currents with different amplitude and durations. The monomers can then be distinguished from the recorded current levels and enhancement/blockage durations.

The monomers can be modified, e.g., labeled with different heavy metal atoms. In this case, the tunneling current on the split-junction electrode is very dependent on the interaction of the labeled heavy metal atoms and the electrode.

Also, the top electrodes are encapsulated by an additional dielectric layer, where via holes are drilled and all electrodes are connected externally for probing. Such a configuration can greatly shorten the interconnect lengths and hence reduce the parasitic capacitance, which accordingly significantly reduces the noise. Such a configuration also minimizes the area occupancy of each functional nanochannel units, and thus allows maximized packing density of sensors on each chip.

Figure 1B:
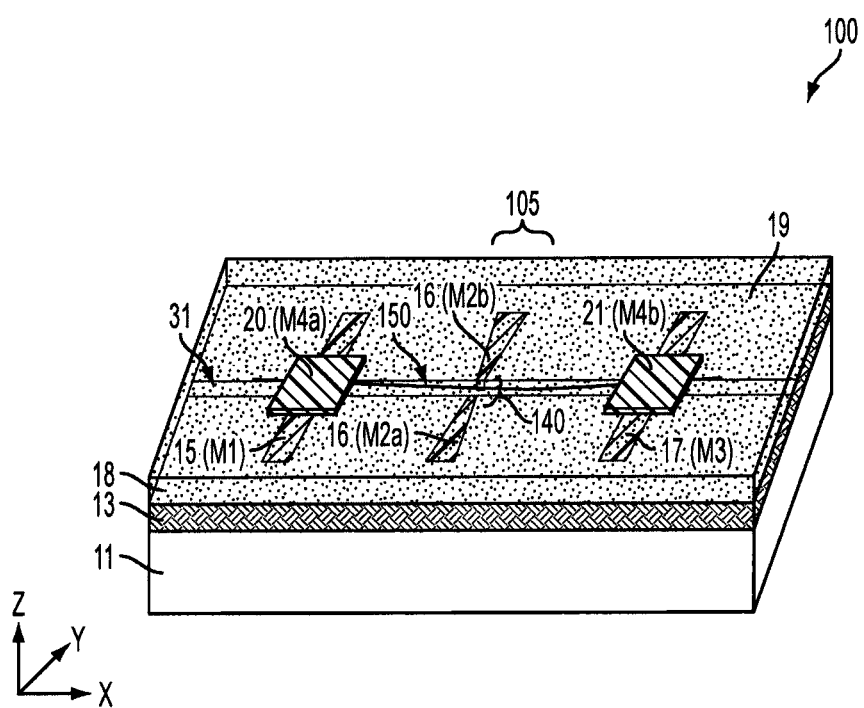
FIG. 1B is a three-dimensional view of the metal insulator channel field effect transistor (MIC-FET) device according to an embodiment.

Now turning to the figures, FIG. 1A is a cross-sectional view of a device 100 and FIG. 1B is a three-dimensional view of the device 100 according to an embodiment. The device 100 is a schematic of a metal insulator channel field effect transistor (MIC-FET). FIGS. 1A and 1B may generally be referred to as FIG. 1.

The device 100 includes a fluidic nanochannel 31 built on a substrate 11 with an insulating coating layer 13, and dielectric coating materials 18 and 19 (e.g., top dielectric coating material and a bottom dielectric coating material) enclosing the nanochannel 31. The dielectric layer 19 is for nanochannel sealing. The device 100 also includes bottom trapping electrode 15 (named M1) and bottom trapping electrode 17 (named M3) crossing the nanochannel 31. Top trapping electrode 20 (named M4a) is aligned to bottom trapping electrode 15 (M1), and top trapping electrode 21 (named M4b) is aligned to bottom trapping electrode 17 (M3). The top trapping electrodes 20 and 21 are separated from the bottom trapping electrodes 15 and 17 by dielectric layers 18 and 19 (which may be the same) and the nanochannel 31. Tunneling electrodes 16 (named M2) is aligned to the nanochannel 31 (at the narrowest location 105) and to accessory microchannel inlets and outlets (not shown). The tunneling electrodes 16 may be referred to as sensing electrodes, tunneling junction electrodes, and split electrodes (because a nanogap is formed between them). The nanochannel 31 is filled with an electrically conductive fluid such as a conductive electrolyte. The electrically conductive fluid can include, e.g., KCl, Tris-Cl, TE buffer, etc.

The device 100 is designed to flow electrically conductive liquid (containing biopolymer molecules) into micro/nano confinement for precise control of the molecules, including trapping them at target positions, manipulating their shapes, and accurately detecting them. The biopolymer molecules can be any linear molecules, including polynucleic acids, e.g., DNA and RNA. A biopolymer molecule 150 is shown in the nanochannel 31 in FIG. 1B. The biopolymer molecule 150 is controlled to be positioned in a nanogap 140 formed between the tunneling electrode 16 which has a left tunneling electrode M2a and a right tunneling electrode M2b for sequentially sensing each base of the molecule 150 that passes in between (by applying a voltage with a voltage source and measuring the current by an ammeter and both may be implemented by a computer 700).

The electrically conductive fluid/liquid can be applied at one side of the device 100 (e.g., in the microchannel inlet) from reservoir 110 and driven to flow through the nanochannel 31 to the other side (and eventually out the microchannel outlet) into reservoir 115. Both reservoirs 110 and 115 are filled with the electrically conductive fluid. Microchannel inlets and outlets connecting the nanochannel 31 are used as both the biopolymer reservoirs and also the interface to contact the external biasing electrodes 120 and 125 in respective reservoirs 110 and 115. The biopolymer molecules 150 are charged in the electrically conductive liquid, and thus can be driven by the electrophoretic force (of the electric field produced by a voltage of a voltage source (which may be implemented by the computer 700) connected to the biasing electrodes 120 and 125) to flow into the nanochannel 31 region, where the manipulation and sensing of the molecules 150 take place.

In the device 100, high-k dielectric materials (e.g., $Al_2O_3$ ($\in_r=9$), $HfO_2$ ($\in_r=25$), $TiO_2$ ($\in_r=80$), etc.), where k is the relative dielectric of the material and $\in$ is the permittivity) are used as the insulating materials for dielectric layers 18 and 19 to enclose the nanochannel 31 and separate the bottom trapping electrodes 15 and 17 from the top trapping electrodes 20 and 21. The biopolymer molecule 150 can be detected once entering into the nanochannel 31 (based on a change in the ionic current level flowing through the nanochannel 31 by the computer 700), and then trapped using a vertical electrical field applied on top and bottom trapping electrodes 20 and 15 (M4a/M1) and/or top and bottom trapping electrodes 21 and 17 (M4b/M3) as further discussed in FIG. 2.

Figure 2A:
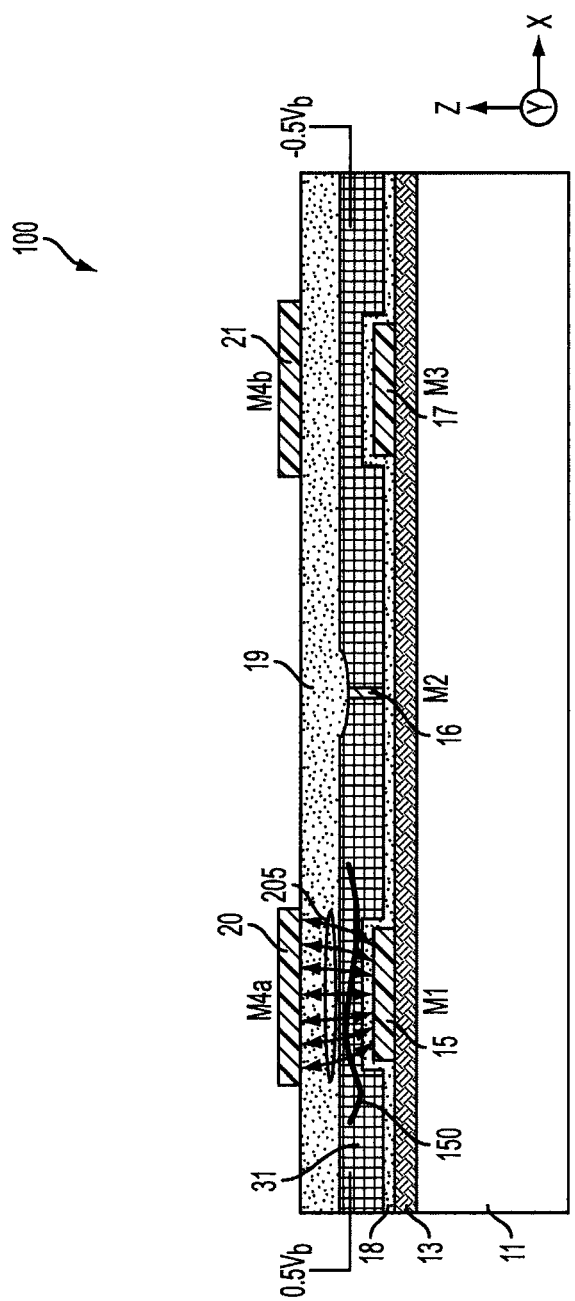
FIG. 2A is a cross-sectional view of a vertical biopolymer trapping mechanism of the metal insulator channel field effect transistor (MIC-FET) device according to an embodiment.
Figure 2B:
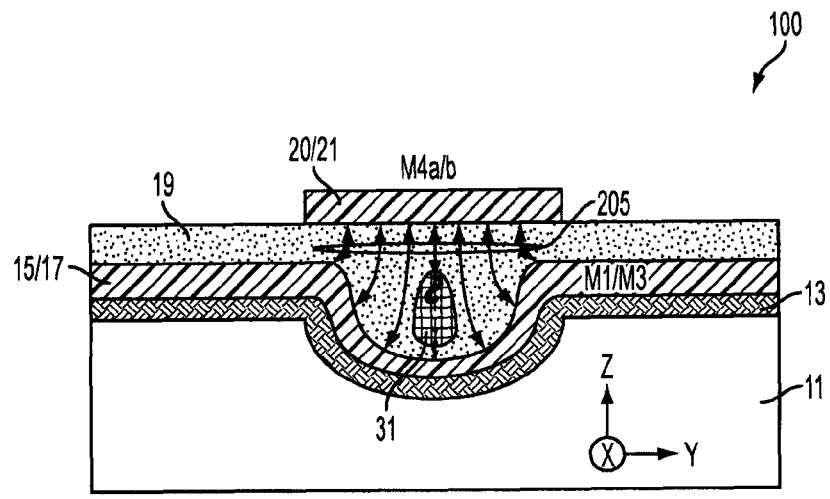
FIG. 2B is a cross-sectional view between top and bottom trapping electrodes for a wrapping bottom trapping electrode according to an embodiment.
Figure 2C:
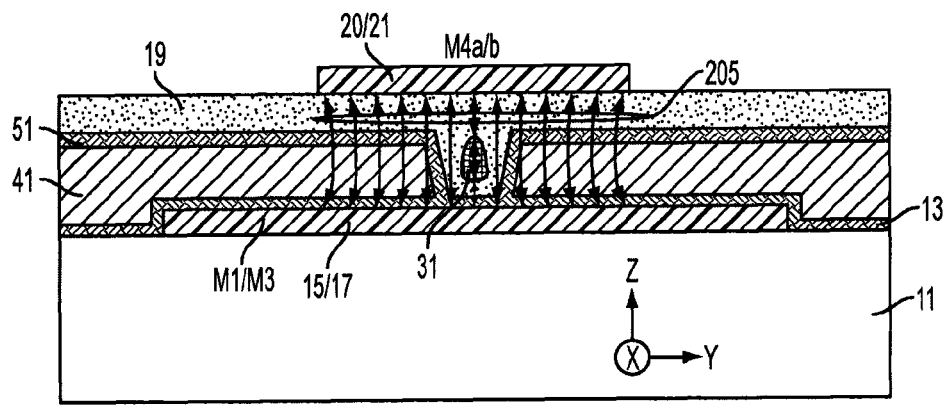
FIG. 2C is a cross-sectional view between top and bottom trapping electrodes for a flat bottom trapping electrode according to an embodiment.

FIGS. 2A, 2B, and 2C illustrate a vertical biopolymer trapping mechanism of the metal insulator channel field effect transistor (MIC-FET) device 100 according to an embodiment. FIG. 2A is a cross-sectional view of the device 100 along the X-Z plane (Y is in the direction of the page). FIG. 2B is a cross-sectional view across the M1 or M3 electrodes along the Y-Z plane to show the geometry of the biopolymer molecule 150 between the top and bottom trapping electrodes for a wrapping bottom trapping electrode M1/M3. FIG. 2C is a cross-sectional view across the M1 or M3 electrodes along the Y-Z plane to show the geometry of the biopolymer molecule 150 between the top and bottom trapping electrodes for a flat bottom trapping electrode M1/M3.

When voltage is applied to the top trapping electrode 20/21 and bottom trapping electrode 15/17, a vertical electric field 205 (shown with up or down arrows depending on the polarity of the applied voltage to the trapping electrode) is produced between the top trapping electrode M4 and the bottom trapping electrode M1/M3 which can trap (press) the biopolymer molecule 150 against either the top dielectric layer 19 or the bottom dielectric layer 18. When the positive voltage is applied to the top trapping electrode M4a/M4b and negative voltage is applied to the bottom trapping electrode M1/M3, the biopolymer molecule 150 is pressed against the bottom dielectric layer 18. Conversely, when negative voltage is applied to the top trapping electrode M4a/M4b and positive voltage is applied to the bottom trapping electrode M1/M3, the biopolymer molecule 150 is pressed against the top dielectric layer 19.

For example, the biopolymer molecule 150 experiences a large electrostatic force to be pushed either upward or downward (via an up or down vertical electrical field 205) to the nanochannel walls (e.g., the dielectric layers 18 and 19), and as a result undergoes a strong friction force against the nanochannel walls, which causes the biopolymer molecule 150 accordingly slow down. The speed of the biopolymer molecule 150 can be reduced to zero, given the fact that the friction force can overcome the electrophoretic force when voltage is applied to the top and bottom trapping electrodes 20 and 15 and/or the top and bottom trapping electrodes 21 and 17. In this case, the biopolymer molecule 150 is trapped inside the overlapping electrode region of the nanochannel 31. Using the planar configuration, the biopolymer molecules 150 can be stained with fluorescent dyes and the trapping behavior can be observed under microscope in real time.

FIG. 2B shows that the vertical electric field 205 lines (through the dielectric layer 19 and the nanochannel 31) press the biopolymer molecule 150 against the top or bottom of the nanochannel 31, for a wrapping bottom electrode of M1 and/or M3.

FIG. 2C shows that the vertical electric field 205 lines (through the dielectric layer 19, a dielectric layer 51, the nanochannel 31, and the dielectric layer 13) to press the biopolymer molecule 150 against the top or bottom of the nanochannel 31, for the flat bottom electrode of M1 and/or M3. To form the flat bottom electrodes, FIG. 2C shows an example in which the bottom trapping electrodes 15 and 17 are deposited directly on the substrate 11 and the dielectric layer 13 is deposited on both the substrate 11 and the bottom trapping electrodes 15 and 17. The dielectric layer 41 is deposited and then etched to form a channel and dielectric layer 51 is deposited.

Figure 3A:
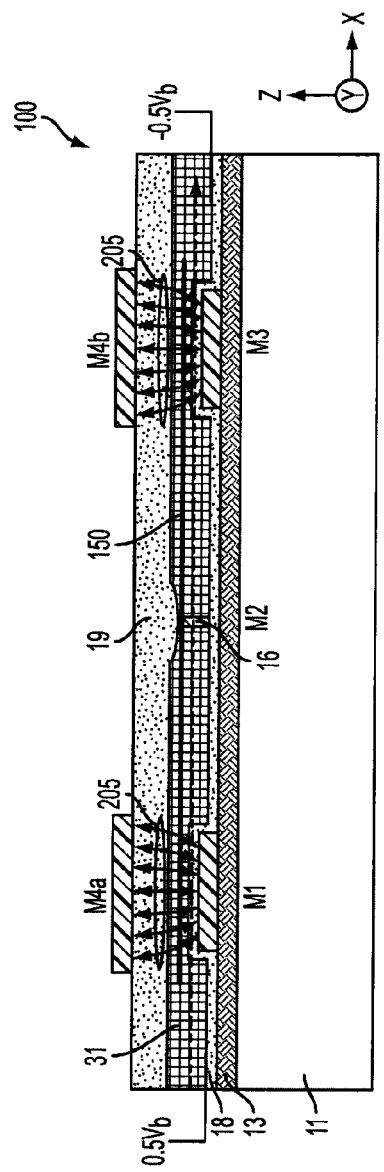
FIG. 3A is a cross-sectional view of the metal insulator channel field effect transistor (MIC-FET) device to illustrate tunneling sensing for the trapped biopolymer molecule according to an embodiment.

FIG. 3A is a cross-sectional view of the device 100 to illustrate DNA tunneling sensing for the trapped biopolymer molecule 150. When M4a and M1 electrodes have trapped the molecule 150, the voltage bias $V_b$ is applied to the biasing electrodes 120 and 125 to drive molecule 150 in the X direction toward M4b and M3 electrodes. The horizontal electric field generated by the voltage bias $V_b$ (which represents 0.5 volts applied to bias electrode 120 and −0.5 volts applied to bias electrode 125) stretches out (i.e., linearizes or uncoils) the coiled biopolymer molecule 150, when the vertical electric field 205 between M4a and M1 holds one end of the molecule 150. The free end of the molecule 150 passes through electrodes M2a and M2b to reach the area between trapping electrodes M4b and M3. When the molecule 150 has been straightened out, voltage can be applied to trapping electrodes M4b and M3 to trap the fee end of the biopolymer molecule 150 (while trapping electrodes M4a and M1 continue holding the left end) such that both ends (left and right) are trapped (held in place). The molecule 150 can now be sensed via sensing electrodes M2a and M2b.

In other words, the opposite forces exert on the trapped molecule 150 unfold and straighten the molecule 150. The device 100, utilizing both vertical electric fields (for trapping the molecule 150) and horizontal electric fields (for moving the molecule 150 horizontally through the nanochannel 31), provides independent control of the different (vertical and horizontal) forces, both in magnitude and direction, and provides flexibility in controlling the position and shape of the targeted biopolymer molecules 150. For example, the voltage applied to trapping electrodes M4a and M1 can be increased to stop the molecule 150 from moving through the nanochannel 31, even when the voltage bias $V_b$ is still being applied to biasing electrodes 120 and 125 (to move the molecule 150 through the nanochannel 31).

Once the molecule 150 is trapped by the vertical electric fields of trapping electrodes M4a and M1 and/or trapping electrodes M4b and M3, the biopolymer molecule 150 straightened in the nanochannel 31 can be measured by applying voltage to the sensing electrodes M2a and M2b (which operate as the nanosensor) as understood by one skilled in the art.

Figure 3B:
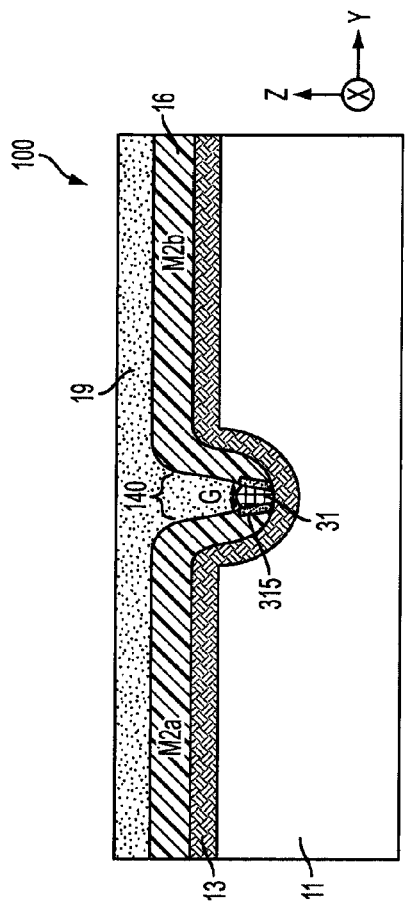
FIG. 3B is a cross-sectional view of the metal insulator channel field effect transistor (MIC-FET) device to illustrate that the tunneling junction electrode has a nanogap between its two electrically isolated parts according to an embodiment.

For molecular sensing, FIG. 3B is a cross-sectional view of the device 100 to illustrate that the tunneling junction electrode 16 (M2a and M2b) has the nanogap 140 (G) aligned to the nanochannel 31 between its two electrically isolated parts (M2a and M2b). The nanogap 140 (G) has a molecular dimension (of, e.g., smaller than 5 nanometers, particularly −2 nanometers) to ensure the detection of a significant tunneling current upon the passage of a base or monomer (on the molecule 150) through the nanogap 140. This is because the tunneling detection is a quantum mechanical process and the current drops exponentially as the nanogap size is increased. The device 100 precisely aligns the nanogap 140 and controls its size down to smaller than 5 nanometers, and thus enables reliable tunneling detection. In one case, the nanogap 140 may be 5-10 nanometers. The detection can be carried out using a sensitive ammeter, possibly in combination with preamplifiers.

As compared to detection using ionic currents, which actually collect a series of base or monomer events, the tunneling currents are much more sensitive, as they reflect the events of the individual bases' or monomers' passage. For more accurate detection, the tunneling electrodes M2a and M2b can be chemically functionalized with coating 315, so that the tunneling signals of the individual bases or monomers of the target biopolymer molecule 150 (e.g., the bases for DNA or RNA molecules) reflect the different characteristic signatures of the bases and monomers. For example, the coating 315 is a self-assembled sensing chemical that is designed to specifically attach to bases and monomers of the target molecule 150 to increase discrimination and detection of the particular bases and monomers. In one embodiment, there can be multiple nanochannels 31 created on the same chip, and the different nanochannels 31 can have nanosensors (i.e., electrodes M2a and M2b) functionalized with different molecules (i.e., different coatings 315). In this case, the same biopolymer molecules 150 can run through the different nanochannels 31 simultaneously for various times, thus quickly collecting large amount of data, which enables statistical study of the biopolymer molecules 150 for fast and accurate identification.

For higher sensitivity, the different bases and monomers can be selectively labeled, e.g., with heavy metal atoms, so that the fingerprint tunneling signals have better contrast from each other.

Figure 3C:
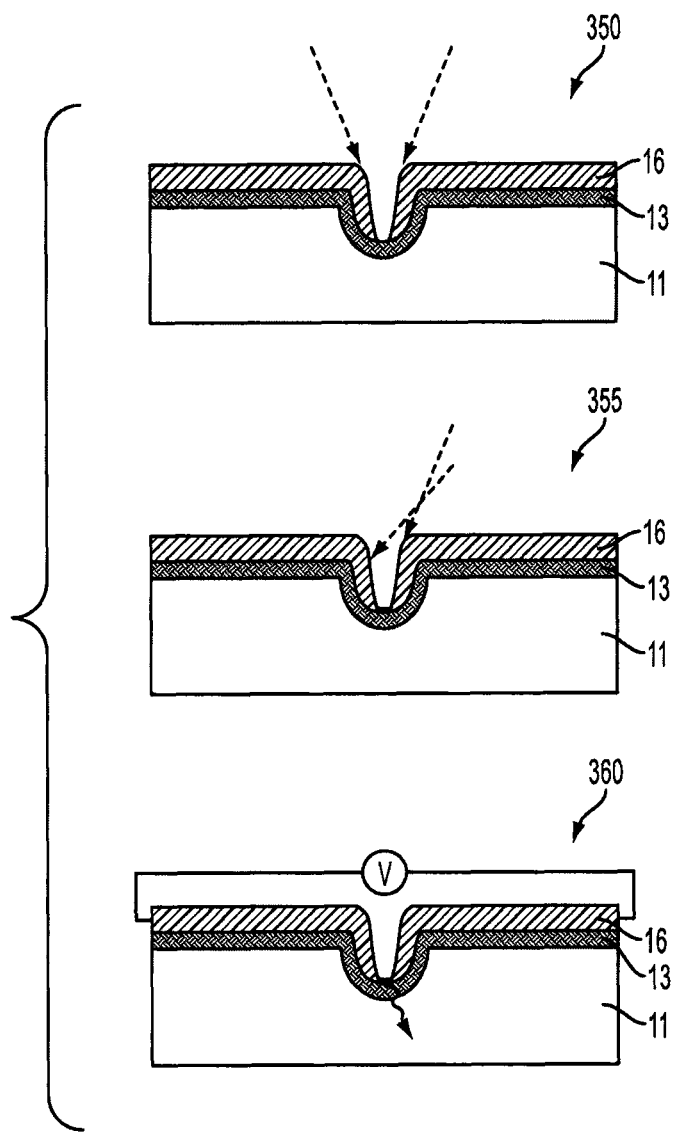
FIG. 3C illustrates two techniques to form the nanogap in the tunneling junction electrode according to an embodiment.

FIG. 3C illustrates two techniques to form the nanogap 140 between the two sensing electrodes 16 shown in the cross-sectional view in FIG. 3B. In FIG. 3C, view 350 shows that the two sensing electrodes 16 (M2a and M2b) can be made by shadow (angle) evaporation. View 355 shows that a single sensing electrode 16 can be made by sputtering, and then view 360 shows that electro-migration with an applied voltage (v) is used to separate the single electrode 16 into two parts (M2a and M2b) while forming the nanogap 140 in between.

Figure 4A:
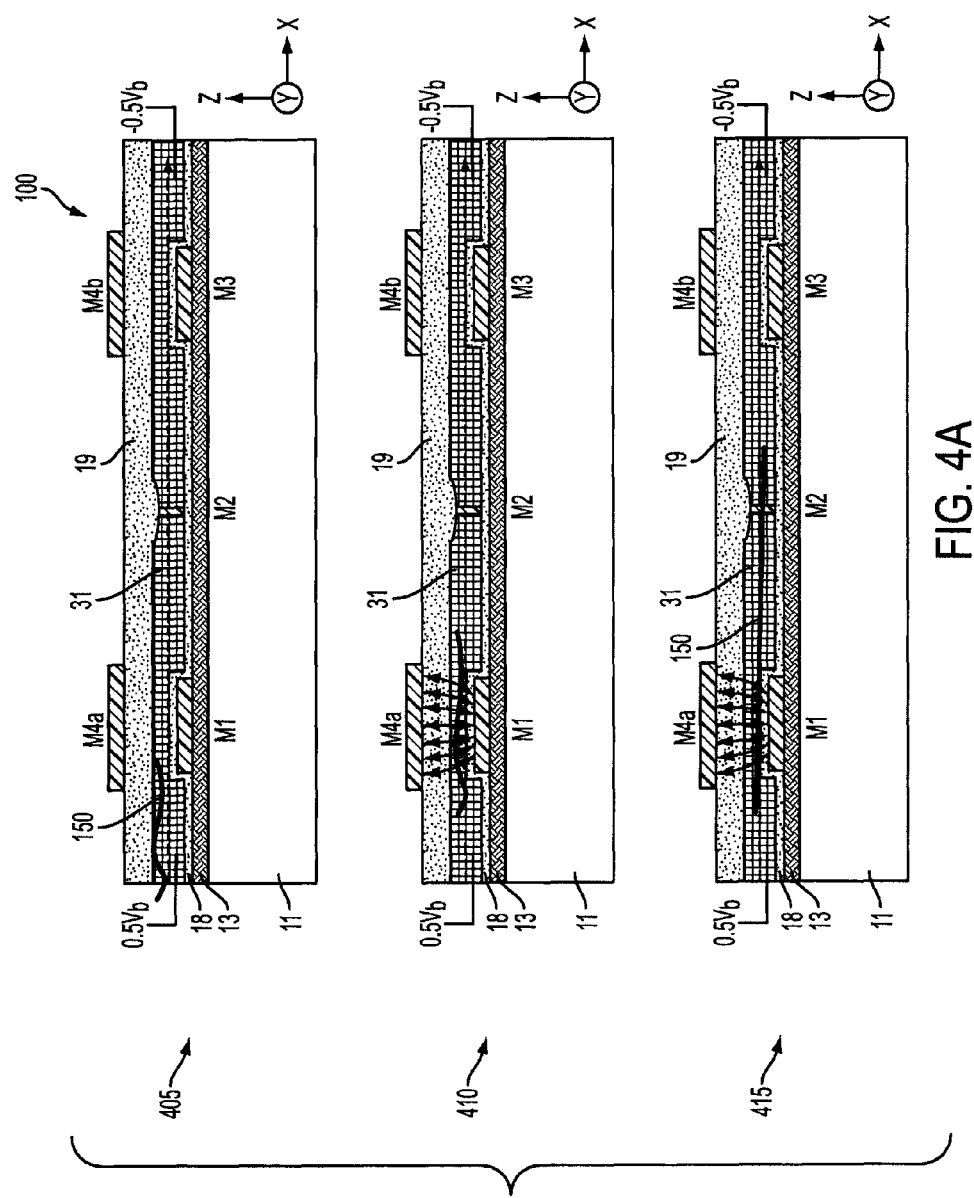
Figure 4B:
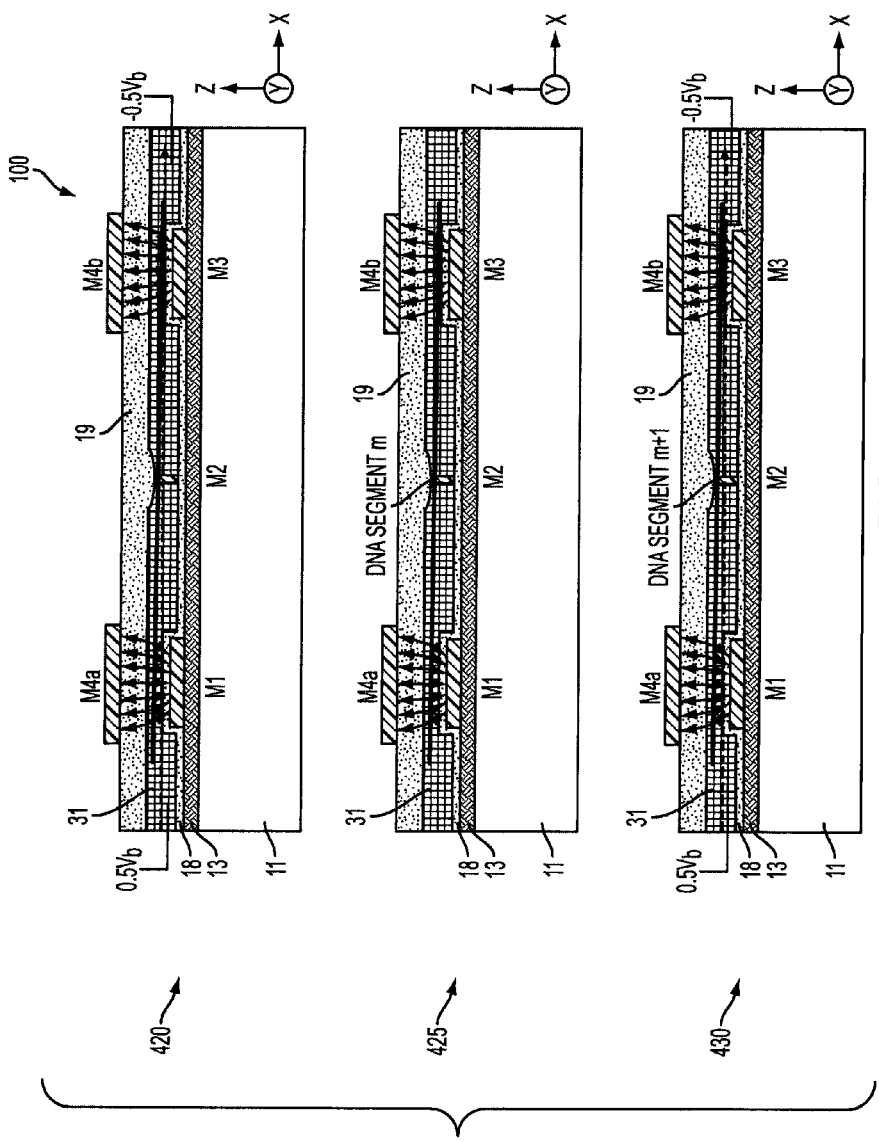
Figure 4C:
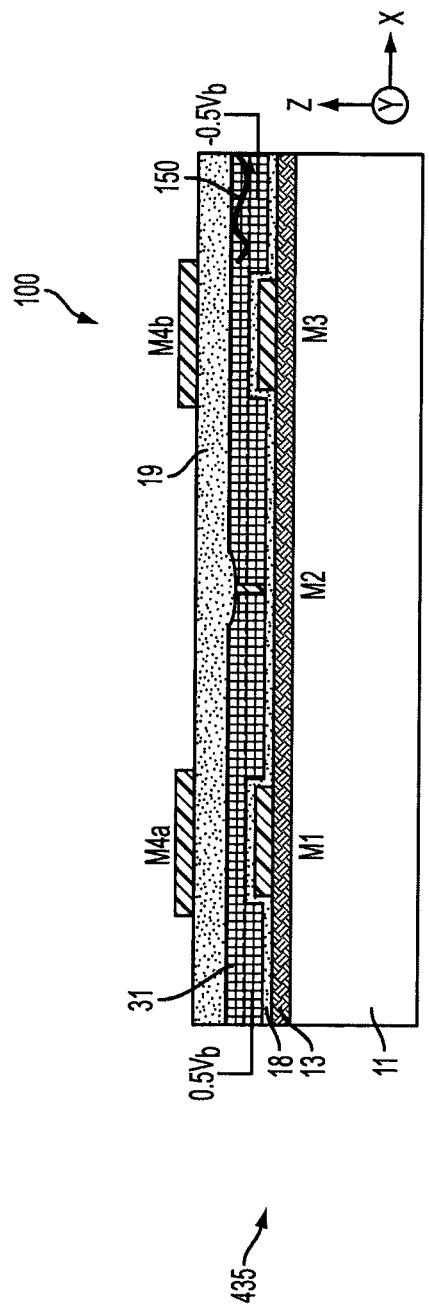

FIGS. 4A, 4B, and 4C illustrate a process of the MIC-FET device 100 for electrical tunneling sequencing. The process by the device 100 is shown as continuing through FIGS. 4A, 4B, and 4C which may generally be referred to as FIG. 4.

The molecule 150 (e.g., DNA) flows in the x-direction (from left to right) driven by the voltage bias $V_b$ (0.5 volts) applied to electrodes 120 and 125 at block 405.

The z-direction vertical trapping potential/voltage is applied on electrodes M1 and M4a (e.g., triggered by ionic current) to stop DNA molecule 150 (by pushing the DNA molecule 150 up or down to causes the friction against the nanochannel 31 wall) at block 410.

At block 415, the x-direction (horizontal) electrical field extends/stretches (via the voltage bias) the DNA molecule 150 in the nanochannel 31 in the x-direction field, while the electrodes M4a and M1 hold the left end of the molecule 150 with the strong vertical trapping electric field (and hence large friction force).

Block 420 shows that the device 100 continues extending DNA molecule 150 into M3/M4b region and the trapping electrodes M3 and M4b are activated (by voltage applied to electrodes M3 and M4b to create the vertical trapping electric filed; to stretch the molecule 150, the device 100 pulses the voltage applied to electrodes M3 and M4b, keeps applying voltage bias $V_b$, and holds the trapping of M1 and M4a by applying voltage to the electrodes M1 and M4a.

Block 425 shows holding the trapping of electrodes M1 and M4a (trap) and electrodes M3 and M4b (trap), removing the voltage bias $V_b$, and reading the DNA base or segment m) in the nanogap 140 by applying voltage to the electrodes M2a and M2b.

Block 430 shows moving the molecule 150 forward by one segment and/or one base (by releasing the trapping electrode M1 and M4a for one voltage pulse while applying voltage bias $V_b$ and while applying voltage to trapping electrodes M3 and M4b), stretching the molecule 150 (by pulsing voltage of the electrode M3 and M4b (trap) while still applying voltage $V_b$ and applying voltage to electrodes M1 and M4a (trap)), and reading DNA segment m+1 of the molecule 150. Block 430 is repeated to finish sequencing all of the bases (e.g., segments m+1 ... to the last segments) of the molecule 150.

Block 435 shows the sequenced DNA is moved away by the x-direction voltage bias $V_b$ force, and the second DNA molecule 150 is to be moved into the nanochannel 31 to be sequenced as discussed above (starting from block 405).

Figure 5A:
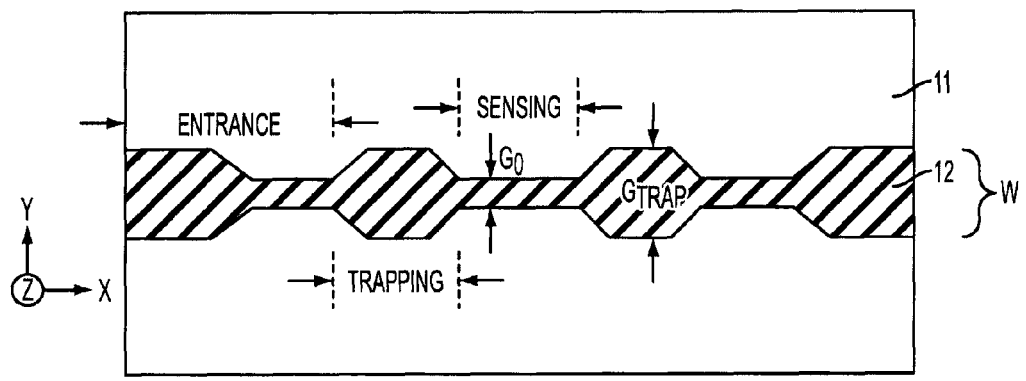

The following is one example of a fabrication process for the device 100. The example fabrication process of the device 100 is shown in FIGS. 5A, 5B, 5C, 5D, and 5E. FIG. 5A is a top view of fabricating nanotrenches in the substrate 11. A recessed channel 12 is shown in the substrate (which will eventually become the nanochannel 31). The trench lateral dimension W can be varied continuously along the length and in a large range (e.g., from a few nanometer to microns or larger). The trench depth can be designed from nanometer scale to microscale or larger. An example of parameters for a narrow trench may be the following: 25 nm (width $G_0$)*50 nm (length)*25 nm (depth). An example of parameters for a wide trench may be the following: 50 nm (width)*50 nm (length) *25 nm (depth).

Figure 5B:
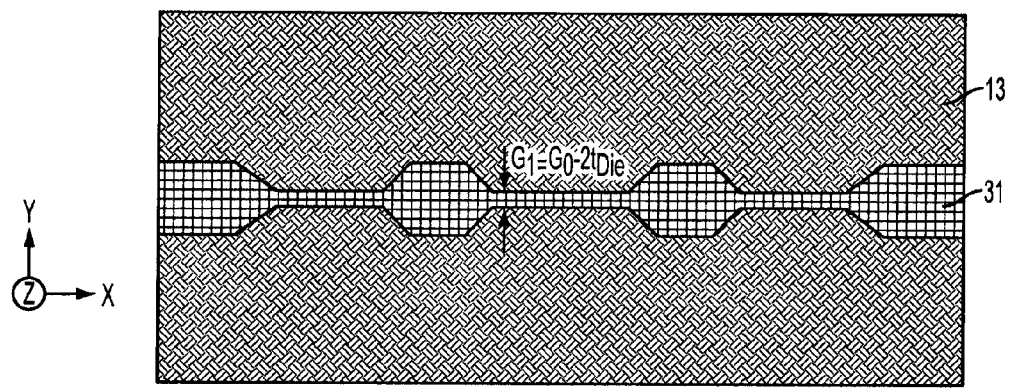

FIG. 5B is a top view of which illustrates reducing the nanotrench size by conformal dielectric deposition. The dielectric coating is deposited on the substrate 11 to form the dielectric layer 13. Now, the recessed channel 12 has the dielectric coating layer 13 inside the channel 12 to reduce its dimensions to the nanochannel 31. The dielectric coating material for dielectric layer 13 may include $SiO_2$, $Si_3N_4$, $Al_2O_3$, $HfO_2$, $TiO_2$, etc. The dielectric coating material also provides chemical functionality. The coating method can be a dry or wet condition. Particularly, a conformal deposition method (e.g., ALD, LPCVD, etc.) may be used.

The dielectric coating material reduces the lateral dimension $G_0$ to $G_1 = G_0 - 2t_{Die}$, where G1 is the new width of the narrowest part of the channel 14 and where $t_{DIE}$ is the dielectric thickness. Note that the conformal coating of the dielectric material deposits everyone including on the channel sidewalls, hence reducing the channel width. An example of the parameters may be the following: deposition thickness ~5 nm applied to reduce the narrow trench width (originally ~25 nm) to ~15 nm.

Figure 5C:
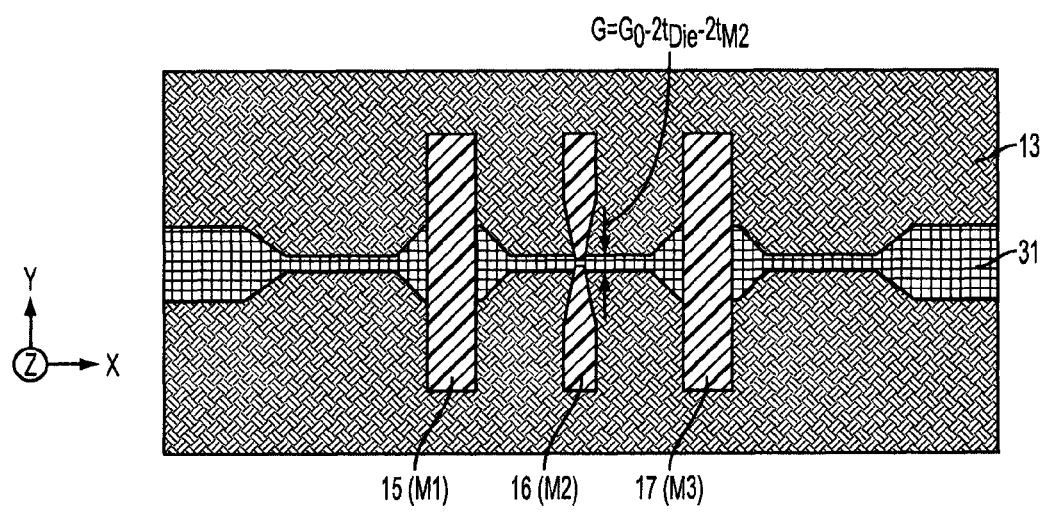

FIG. 5C is a top view which illustrates deposition of metals M1, M2, and M3 over the nanochannel 31. The metals are conducting material to form electrodes 15, 16, and 17.

The geometry (e.g., shape, length, width, thickness) of metals M1, M2, and M3 can be different. The material of metals M1, M2, and M3 can be different from each other for different functions. The material of metals M1, M2, and M3 can be deposited individually, and surface modified chemically or by other means. Metals M1 and M3 may be a group of lateral electrodes for stretching and ratcheting DNA molecule 150.

An example of parameters for the metals may be the following: metal thickness ~5 nm, M2 width 5 nm (target), M1 and M3 width ~40 nm. For a narrow trench, width G at M2 is further reduced to ~5 nm. Spacing of adjacent electrodes (e.g., between M1 and M2 and M3) is ~50 nm.

Figure 5D:
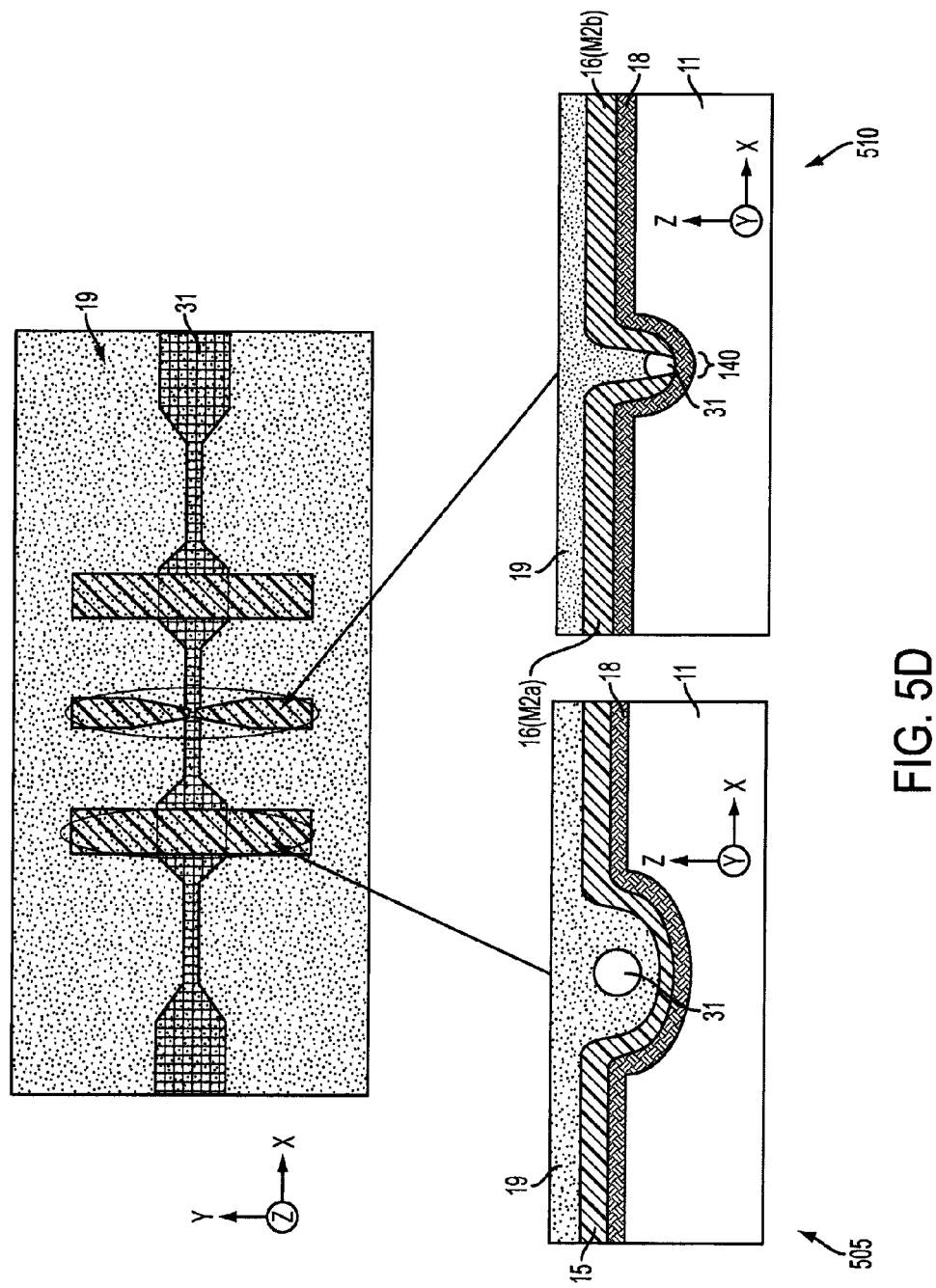

FIG. 5D is a top view which illustrates sealing of the nanochannel 31 with a top-gate dielectric material 19. An insulating material for the dielectric layer 19 is used for sealing the nanochannel 31. The material also provides the field control of trapping DNA.

Block 505 illustrates a cross-sectional view of the metal M1 (which applies to the metal M3) sealed under the dielectric layer 19 while block 510 illustrates a cross-sectional view of the metal M2a and M2b sealed under the dielectric layer 19.

Figure 5E:
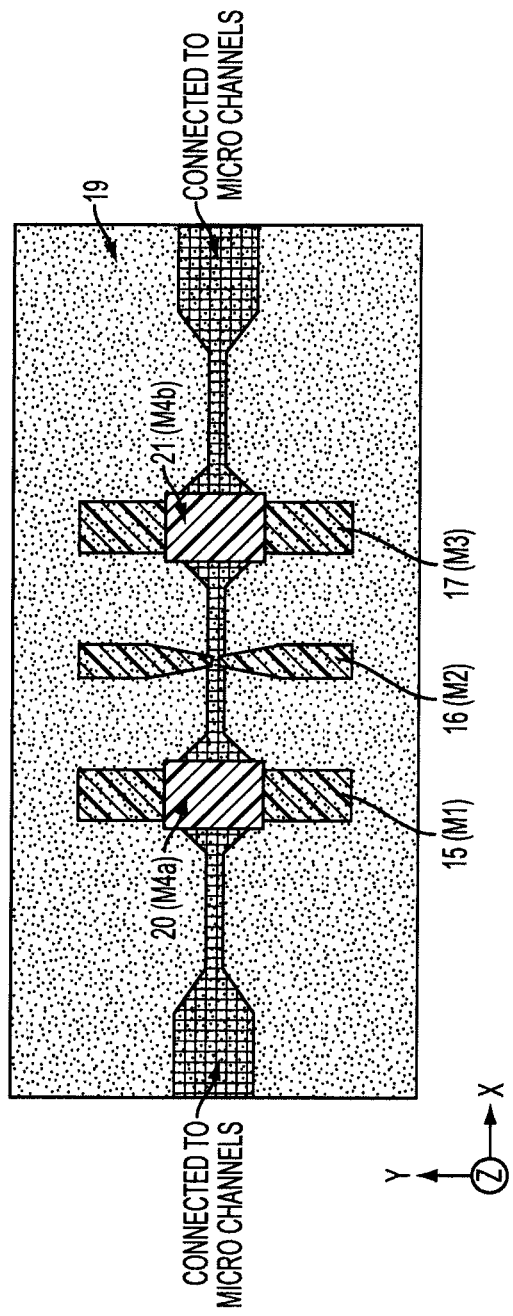

FIG. 5E is a top view which illustrates deposition of the top gate M4. The metal M4a and M4b are the top gate material used for the molecular manipulation. M4 can be the same as or different from the material for M1, M2, and M3. M4, as vertical trapping electrodes 20 and 21, provides the vertical electric control of the charged molecule 150 in the overlap region with M1 and M3 respectively. M4 can be designed as connected lines or separated lines in geometry.

FIG. 5E also illustrates micro channels, such as the micro inlet (left) and micro outlet right, which are operatively connected to the reservoirs 110 and 115 as understood by one skilled in the art.

Figure 6:
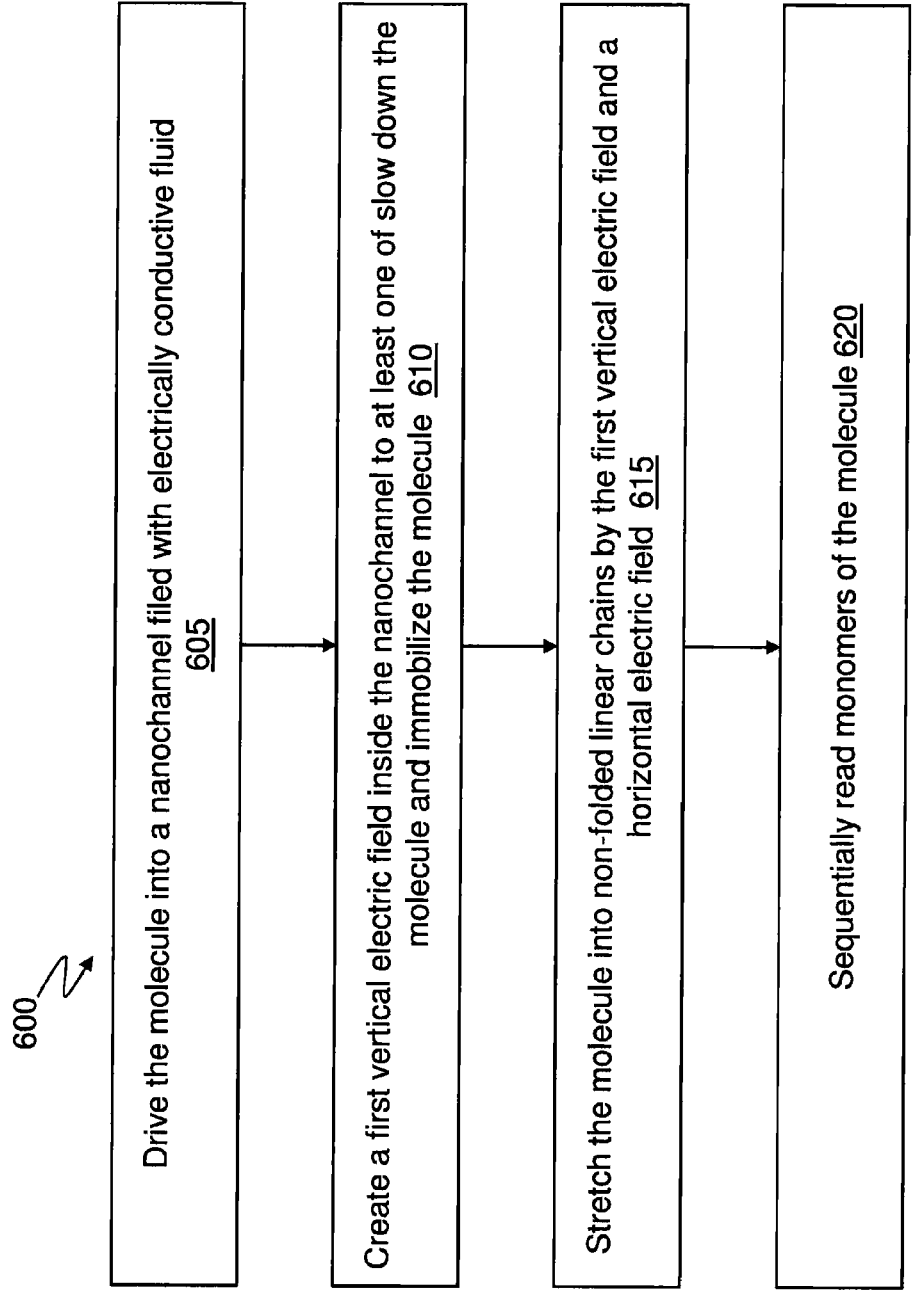
FIG. 6 is a method for manipulating and sensing the molecule in the nanochannel of the metal insulator channel field effect transistor (MIC-FET) device according to an embodiment.

FIG. 6 is a method 600 for manipulating and sensing the molecule 150 in the nanochannel 31 of the device 100. Reference can be made to FIGS. 1-5 (along with FIG. 7 discussed below).

At block 605, the voltage bias of the biasing electrodes 120 and 125 drives the molecule 150 (from the reservoir 110) into the nanochannel 31 filed with electrically conductive fluid.

The trapping electrodes 15 and 20 create a first vertical electric field (e.g., vertical electric filed 205) inside the nanochannel 31 to at least slow down the molecule and immobilize the molecule 150 in the nanochannel 31 at block 610.

At block 615, the molecule 150 is stretched into non-folded linear chains by the first vertical electric field of the trapping electrodes 15 and 20 and a horizontal electric field of the electrodes 120 and 125. The sensing electrodes 16 sequentially read monomers (via a connection to a voltage source and ammeter) of the molecule 150 at block 620.

The method in which the first vertical electric field 205 (by trapping electrodes M1 and M4*a*) immobilizes the molecule 150 before contacting a nanogap 140 (between sensing electrodes M2*a* and M2*b*) in which the molecule 150 is sensed for reading. The method in which the first vertical electric field holds a first end of the molecule 150 while a second end is free (e.g., block 410 and 415). The method in which the second end of the molecule 150 stretches as the first end of the molecule is being held by the trapping electrodes M1 and M4*a* (e.g., block 415). The method in which the horizontal electric field (by electrodes 120 and 125) causes the molecule 150 to stretch while the first end is held by the vertical electric field until the molecule 150 is straighten (e.g., block 415). The method in which the molecule 150 is held by a second vertical electric field (of the trapping electrodes M3 and M4*b*) at or near the second end of the molecule 150 when reading the monomers (e.g., blocks 420 and 425).

The method moves the molecule 150 forward by one segment, which comprises: applying the first vertical electric field to hold the molecule at a first end and applying a second vertical electric field to hold the molecule at a second end (blocks 420 and 425), releasing the first vertical electric field at the first end for one pulse while applying the horizontal electric field to drive the molecule forward by one segment and while holding the molecule 150 at the second end (block 425 and 430), stretching the molecule by applying the horizontal electric field and applying the first vertical electric field while releasing the second electric field for one pulse (block 415 and 425), and reading the molecule 150 increased by one segment (block 430).

The method in which the first vertical electric field is generated by a first pair of trapping electrodes M1 and M4*a* positioned to the nanochannel 31, and the second vertical electric field is generated by a second pair of trapping electrodes M3 and M4*b* positioned to the nanochannel 31 at an area distinct from the first pair of trapping electrodes. The method in which the first vertical electric field causes forces to pin the molecule against a wall (e.g., the bottom or top depending on the polarity) of the nanochannel 31, and the second vertical electric field causes forces to pin the molecule 150 against a wall (e.g., the bottom or top depending on the polarity) of the nanochannel 31.

The method in which the molecule 150 is a deoxyribonucleic acid and the monomers are bases of the deoxyribonucleic acid. The method in which the molecule is a ribonucleic acid and the monomers are bases of the ribonucleic acid.

Figure 7:
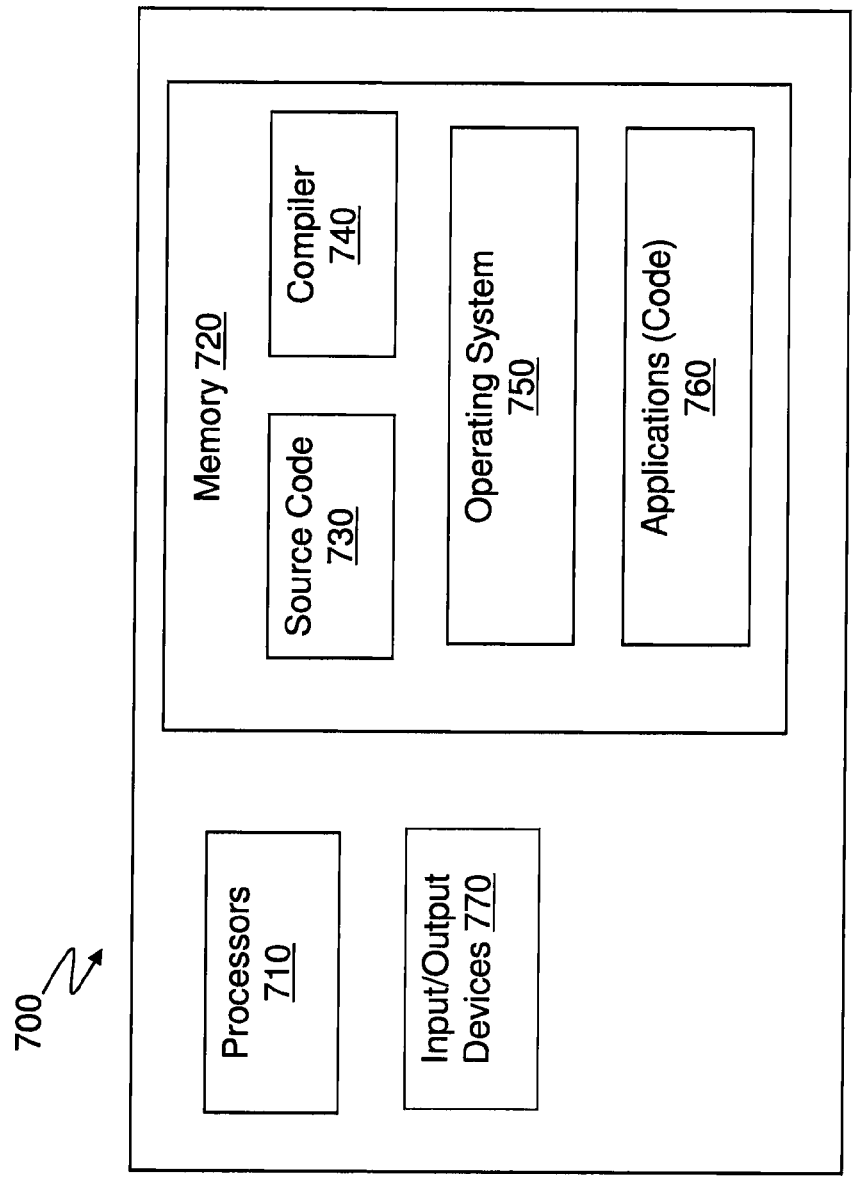
FIG. 7 is a block diagram that illustrates an example of a computer (computer setup) having capabilities, which may be included in and/or combined with embodiments.

FIG. 7 illustrates an example of a computer 700 (e.g., as part of the computer setup for testing and analysis) which may implement, control, and/or regulate the voltages applied by respective voltage sources individually connected to trapping electrodes 15 and 20, trapping electrodes 17 and 21, sensing electrodes 16, biasing electrodes 120 and 125. The computer 700 may implement, control, and/or regulate (current) measurements of respective ammeters individually connected to trapping electrodes 15 and 20, trapping electrodes 17 and 21, sensing electrodes 16, biasing electrodes 120 and 125.

Various methods, procedures, modules, flow diagrams, tools, applications, circuits, elements, and techniques discussed herein may also incorporate and/or utilize the capabilities of the computer 700. Moreover, capabilities of the computer 700 may be utilized to implement features of exemplary embodiments discussed herein. One or more of the capabilities of the computer 700 may be utilized to implement, to connect to, and/or to support any element discussed herein (as understood by one skilled in the art) in FIGS. 1-6. For example, the computer 700 which may be any type of computing device and/or test equipment (including ammeters, voltage sources, connectors, etc.). Input/output device 770 (having proper software and hardware) of computer 700 may include and/or be coupled to the nanodevices and structures discussed herein via cables, plugs, wires, electrodes, patch clamps, etc. Also, the communication interface of the input/output devices 770 comprises hardware and software for communicating with, operatively connecting to, reading, and/or controlling voltage sources, ammeters, and current traces (e.g., magnitude and time duration of current), etc., as discussed herein. The user interfaces of the input/output device 770 may include, e.g., a track ball, mouse, pointing device, keyboard, touch screen, etc., for interacting with the computer 700, such as inputting information, making selections, independently controlling different voltages sources, and/or displaying, viewing and recording current traces for each base, molecule, biomolecules, etc.

Generally, in terms of hardware architecture, the computer 700 may include one or more processors 710, computer readable storage memory 720, and one or more input and/or output (I/O) devices 770 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 710 is a hardware device for executing software that can be stored in the memory 720. The processor 710 can be virtually any custom made or commercially available processor, a central processing unit (CPU), a data signal processor (DSP), or an auxiliary processor among several processors associated with the computer 700, and the processor 710 may be a semiconductor based microprocessor (in the form of a microchip) or a macroprocessor.

The computer readable memory 720 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 720 may incorporate electronic, magnetic, optical, and/or other types of storage media. Note that the memory 720 can have a distributed architecture, where various components are situated remote from one another, but can be accessed by the processor 710.

The software in the computer readable memory 720 may include one or more separate programs, each of which comprises an ordered listing of executable instructions for implementing logical functions. The software in the memory 720 includes a suitable operating system (O/S) 750, compiler 740, source code 730, and one or more applications 760 of the exemplary embodiments. As illustrated, the application 760 comprises numerous functional components for implementing the features, processes, methods, functions, and operations of the exemplary embodiments.

The operating system 750 may control the execution of other computer programs, and provides scheduling, input-output control, file and data management, memory management, and communication control and related services.

The application 760 may be a source program, executable program (object code), script, or any other entity comprising a set of instructions to be performed. When a source program, then the program is usually translated via a compiler (such as the compiler 740), assembler, interpreter, or the like, which may or may not be included within the memory 720, so as to operate properly in connection with the O/S 750. Furthermore, the application 760 can be written as (a) an object oriented programming language, which has classes of data and methods, or (b) a procedure programming language, which has routines, subroutines, and/or functions.

The I/O devices 770 may include input devices (or peripherals) such as, for example but not limited to, a mouse, keyboard, scanner, microphone, camera, etc. Furthermore, the I/O devices 770 may also include output devices (or peripherals), for example but not limited to, a printer, display, etc. Finally, the I/O devices 770 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 770 also include components for communicating over various networks, such as the Internet or an intranet. The I/O devices 770 may be connected to and/or communicate with the processor 710 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 760 is implemented in hardware, the application 760 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for manipulating a molecule, the method comprising:
   driving the molecule into a nanochannel filed with electrically conductive fluid;
   creating, by a first pair of trapping electrodes, a first vertical electric field inside the nanochannel to at least one of: slow down the molecule and immobilize the molecule;
   wherein the first pair of trapping electrodes are positioned to the nanochannel and comprise a first top electrode and a first bottom electrode;
   wherein a top high-k dielectric material separates the nanochannel from the first top electrode, such that the first top electrode does not form the nanochannel; and
   wherein a bottom high-k dielectric material separates the nanochannel from the first bottom electrode, such that the first bottom electrode does not form the nanochannel;
   stretching the molecule into non-folded linear chains by the first vertical electric field and a horizontal electric field; and
   sequentially reading monomers of the molecule.

2. The method of claim 1, wherein the first vertical electric field immobilizes the molecule before the molecule contacts a nanogap in which the molecule is sensed for reading.

3. The method of claim 1, wherein the first vertical electric field holds a first end of the molecule while a second end is free.

4. The method of claim 3, wherein the second end of the molecule stretches as the first end of the molecule is being held.

5. The method of claim 4, wherein the horizontal electric field causes the molecule to stretch while the first end is held by the first vertical electric field until the molecule is straightened.

6. The method of claim 5, wherein the molecule is held by a second vertical electric field at or near the second end of the molecule when reading the monomers, the second vertical electric field created by a second pair of trapping electrodes;
   wherein the second pair of trapping electrodes are positioned to the nanochannel and comprise a second top electrode and a second bottom electrode;
   wherein the top high-k dielectric material separates the nanochannel from the second top electrode, such that the second top electrode does not form the nanochannel; and
   wherein the bottom high-k dielectric material separates the nanochannel from the second bottom electrode, such that the second bottom electrode does not form the nanochannel.

7. The method of claim 1, further comprising moving the molecule forward by one segment, which comprises:
   applying the first vertical electric field to hold the molecule at a first end and applying a second vertical electric field to hold the molecule at a second end;
   releasing the first vertical electric field at the first end for one pulse while applying the horizontal electric field to drive the molecule forward by one segment and while holding the molecule at the second end;

stretching the molecule by applying the horizontal electric field and applying the first vertical electric field while releasing the second vertical electric field for one pulse; and reading the molecule increased by one segment.

8. The method of claim 7, wherein the first vertical electric field is generated by the first pair of trapping electrodes positioned to the nanochannel.

9. The method of claim 8, wherein the second vertical electric field is generated by the second pair of trapping electrodes positioned to the nanochannel at an area distinct from the first pair of trapping electrodes.

10. The method of claim 7, wherein the horizontal electric field is generated by a pair of electrodes.

11. The method of claim 7, wherein the first vertical electric field causes forces to pin the molecule against a wall of the nanochannel.

12. The method of claim 7, wherein the second vertical electric field causes forces to pin the molecule against a wall of the nanochannel.

13. The method of claim 1, wherein the molecule is a deoxyribonucleic acid and the monomers are bases of the deoxyribonucleic acid.

14. The method of claim 1, wherein the molecule is a ribonucleic acid and the monomers are bases of the ribonucleic acid.

* * * * *